(12) United States Patent
Locke et al.

(10) Patent No.: US 9,446,176 B2
(45) Date of Patent: *Sep. 20, 2016

(54) DRESSINGS AND METHODS FOR TREATING A TISSUE SITE ON A PATIENT

(71) Applicant: KCI Licensing, Inc., San Antonio, TX (US)

(72) Inventors: Christopher Brian Locke, Bournemouth (GB); Timothy Mark Robinson, Basingstoke (GB); Aidan Marcus Tout, Alderbury (GB)

(73) Assignee: KCI Licensing, Inc., San Antonio, TX (US)

( * ) Notice: Subject to any disclaimer, the term of this patent is extended or adjusted under 35 U.S.C. 154(b) by 19 days.

This patent is subject to a terminal disclaimer.

(21) Appl. No.: 14/075,864

(22) Filed: Nov. 8, 2013

(65) Prior Publication Data

US 2014/0066867 A1    Mar. 6, 2014

Related U.S. Application Data

(63) Continuation of application No. 13/084,813, filed on Apr. 12, 2011, now Pat. No. 8,604,265.

(60) Provisional application No. 61/359,181, filed on Jun. 28, 2010, provisional application No. 61/359,205, filed on Jun. 28, 2010, provisional application No. 61/325,115, filed on Apr. 16, 2010.

(51) Int. Cl.
*A61F 13/00* (2006.01)
*A61M 1/00* (2006.01)
*A61F 13/02* (2006.01)

(52) U.S. Cl.
CPC ............ *A61M 1/0023* (2013.01); *A61F 13/02* (2013.01); *A61F 13/0216* (2013.01);

(58) Field of Classification Search
CPC ...... A01N 25/34; A01N 25/10; A01N 33/12; A01N 47/44; A61L 2300/404; A61L 15/46; A61L 2300/206; A61L 2300/208; A61L 2300/606; A61L 15/44; A61L 2300/406; A61L 2300/45; A61F 13/00068
USPC .............. 604/317–327, 540, 543; 602/46–54
See application file for complete search history.

(56) References Cited

U.S. PATENT DOCUMENTS 1,355,846 A    10/1920  Rannells
2,547,758 A    4/1951   Keeling (Continued)

FOREIGN PATENT DOCUMENTS

AU    550575 A1    3/1986
AU    745271        4/1999

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Michael Brown

(57) ABSTRACT

Dressings, systems, and methods for treating a tissue site on a patient involve allowing liquids from the tissue site or a priming fluid to evaporate and exit the dressing through a liquid-impermeable, vapor-permeable membrane. The dressing is able to process more liquids than would otherwise be possible without evaporation and potentially to create reduced pressure. Other dressings, systems, and methods are disclosed.

38 Claims, 5 Drawing Sheets

(52) U.S. Cl.
CPC ...... *A61F 13/0223* (2013.01); *A61F 13/0226* (2013.01); *A61M 1/0001* (2013.01); *A61M 1/009* (2014.02); *A61M 1/0031* (2013.01); *A61M 1/0052* (2014.02); *A61M 1/0088* (2013.01); *A61F 2013/0074* (2013.01); *A61F 2013/00536* (2013.01); *A61M 1/0058* (2013.01); *A61M 1/0066* (2013.01); *A61M 2205/7527* (2013.01); *A61M 2205/7536* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,599,289 A * | 2/1997 | Castellana ............ A61F 13/023 128/853 |
| 5,607,388 A | 3/1997 | Ewall |
| 5,636,643 A | 6/1997 | Argenta et al. |
| 5,645,081 A | 7/1997 | Argenta et al. |
| 5,759,570 A * | 6/1998 | Arnold ................ A61F 13/0203 424/443 |
| 6,011,194 A * | 1/2000 | Buglino ............... A61F 13/0209 428/326 |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0136773 A1* | 6/2005 | Yahiaoui ............... A61F 13/537 442/394 |
| 2009/0024067 A1* | 1/2009 | Siniaguine ........ A61F 13/00995 602/43 |

FOREIGN PATENT DOCUMENTS

| | | | |
|---|---|---|---|
| AU | 755496 | 2/2002 | |
| CA | 2005436 | 6/1990 | |
| DE | 26 40 413 A1 | 3/1978 | |
| DE | 43 06 478 A1 | 9/1994 | |
| DE | 295 04 378 U1 | 10/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 B1 | 8/2004 | |
| GB | 692578 | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 B | 3/1999 | |
| GB | 2 333 965 A | 8/1999 | |
| GB | WO2009066106 | * 5/2009 | ............. A61F 13/02 |
| JP | 4129536 | 4/1992 | |
| SG | 71559 | 4/2002 | |
| WO | 80/02182 | 10/1980 | |
| WO | 87/04626 | 8/1987 | |
| WO | 90/010424 | 9/1990 | |
| WO | 93/09727 | 5/1993 | |
| WO | 94/20041 | 9/1994 | |
| WO | 96/05873 | 2/1996 | |
| WO | 97/18007 | 5/1997 | |

(56) References Cited

FOREIGN PATENT DOCUMENTS

| WO | 99/13793 | 3/1999 |
|---|---|---|
| WO | 2005025447 A2 | 3/2005 |
| WO | 2009111655 A2 | 9/2009 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/the British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).

* cited by examiner

DRESSINGS AND METHODS FOR TREATING A TISSUE SITE ON A PATIENT

RELATED APPLICATION

This application is a Continuation of U.S. patent application Ser. No. 13/084,813, entitled "Dressings and Methods For Treating A Tissue Site On A Patient", filed 12 Apr. 2011, which claims the benefit, under 35 USC §119(e), of the filing of U.S. Provisional Patent Application Ser. No. 61/359,181, entitled "Dressings and Methods For Treating a Tissue Site On A Patient," filed 28 Jun. 2010, which is incorporated herein by reference for all purposes; U.S. Provisional Patent Application Ser. No. 61/359,205, entitled "Evaporative Body Fluid Containers and Methods," filed 28 Jun. 2010, which is incorporated herein by reference for all purposes; and, U.S. Provisional Patent Application Ser. No. 61/325,115, entitled "Reduced-Pressure Sources, Systems, and Methods Employing A Polymeric, Porous, Hydrophobic Material," filed 16 Apr. 2010; which is incorporated herein by reference for all purposes.

BACKGROUND

The present disclosure relates generally to medical treatment systems and, more particularly, but not by way of limitation, to dressings, methods, and systems for treating a tissue site on a patient.

Clinical studies and practice have shown that providing reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. It is believed that treatment of low-severity wounds with reduced pressure will yield benefits as well, but issues remain.

SUMMARY

According to an illustrative embodiment, a dressing for treating a tissue site on a patient includes a wound interface member for placing proximate to the tissue site and a covering. At least a portion of the covering comprises an evaporative window having a liquid-impermeable, vapor-permeable membrane. The covering is operable to form a sealed space over the tissue site. The liquid-impermeable, vapor-permeable membrane allows evaporated liquids, e.g., water vapor or a priming fluid, in the sealed space to egress the sealed space. The egress of evaporated liquids may create a reduced pressure in the sealed space.

According to an illustrative embodiment, a method for treating a tissue site with reduced pressure includes placing a wound interface member proximate to the tissue site and covering the wound interface member with a covering having an evaporative window. The evaporative window comprises a liquid-impermeable, vapor-permeable membrane. The covering forms a sealed space over the wound interface member. The method further includes allowing liquids from the tissue site to evaporate and to egress the sealed space through the liquid-impermeable, vapor-permeable membrane. The evaporation may cause a reduced pressure to be created in the sealed space.

According to still another illustrative embodiment, a method of manufacturing a dressing for treating a tissue site includes providing a foam member for placing proximate to the tissue site, providing a covering formed with an evaporative-window opening, and associating a liquid-impermeable, vapor-permeable membrane with the evaporative-window opening to form an evaporative window. The liquid-impermeable, vapor-permeable membrane is operable to allow evaporated liquids to be transmitted through the liquid-impermeable, vapor-permeable membrane.

Other features and advantages of the illustrative embodiments will become apparent with reference to the drawings and detailed description that follow

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
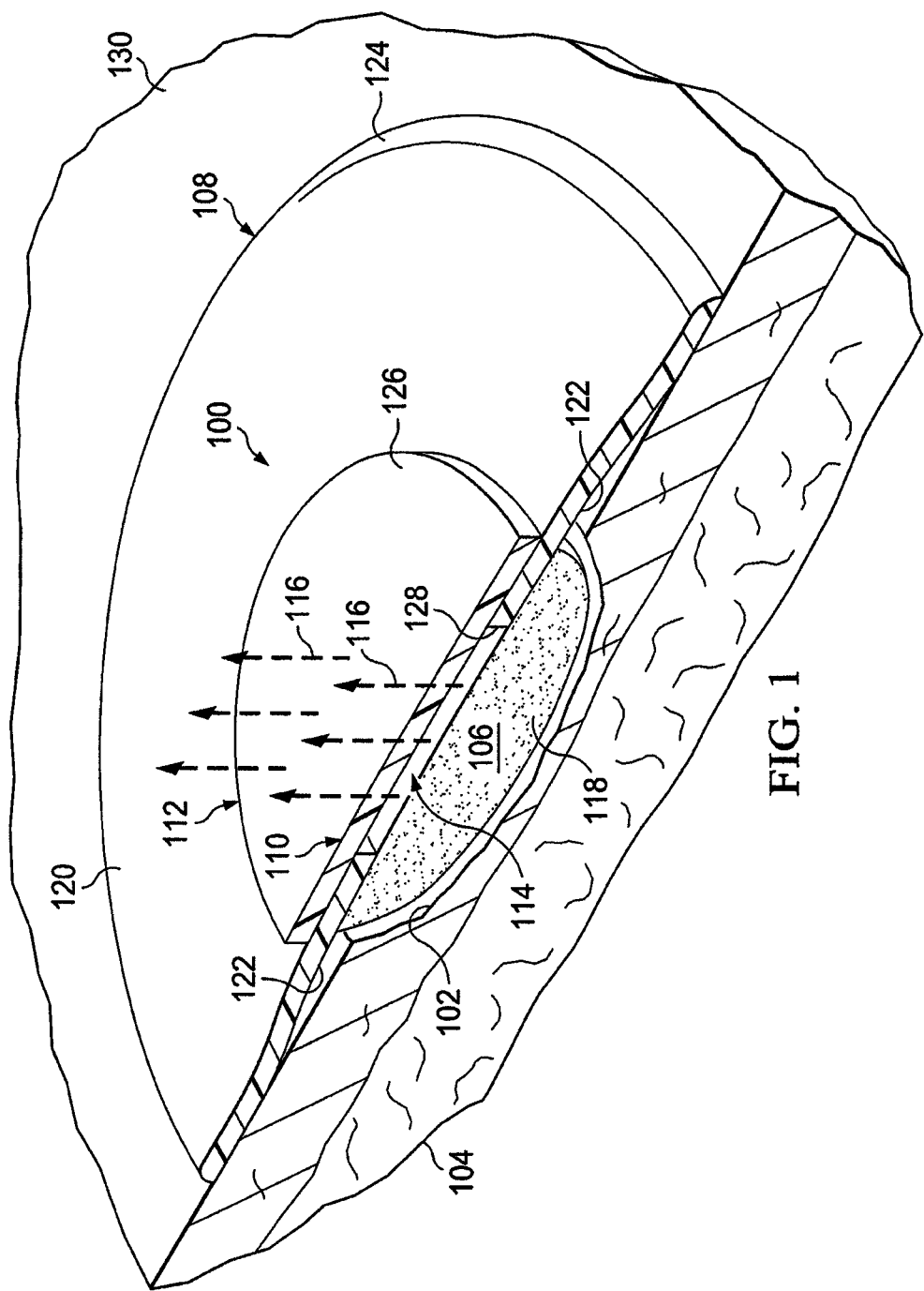
FIG. 1 is a schematic, perspective view, with a portion shown in cross section, of an illustrative embodiment of a dressing for treating a tissue site.

Referring to the drawings and initially to FIG. 1, a dressing 100 for treating a tissue site 102 on a patient 104 is presented. The dressing 100 includes, inter alia, a covering 108 that allows evaporated liquids to egress the dressing 100. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue.

The dressing 100 includes a wound interface member, such as a foam member 106 or gauze, for placing proximate to the tissue site 102. The dressing 100 also includes the covering 108. At least a portion of the covering 108 is formed with an evaporative-window opening or aperture 128 covered by a liquid-impermeable, vapor-permeable membrane 112 to form an evaporative window 110. The covering 108 forms a sealed space 114 over the tissue site 102 and the foam member 106. The liquid-impermeable, vapor-permeable membrane 112 is operable to allow liquids, e.g., water, in the sealed space 114 that have evaporated to egress the sealed space 114 as suggested by arrows 116. For example, body fluids from the tissue site 102 may be drawn into the foam member 106 and water from the body fluids may evaporate to form water vapor that egresses the sealed space 114 through the liquid-impermeable, vapor-permeable membrane 112.

The foam member 106 may be placed proximate to the tissue site 102 and helps to remove liquids, e.g., body fluids, from the tissue site 102 when under the influence of reduced pressure and may help distribute reduced pressure to the tissue site 102. Thus, the foam member 106 serves as a manifold. The term "manifold" as used herein generally refers to a substance or structure that is provided to assist in applying reduced pressure to, delivering fluids to, or removing fluids from the tissue site 102. The foam member 106, or manifold, typically includes a plurality of flow channels or pathways that distribute fluids provided to and removed from the tissue site 102 around the foam member 106. In one illustrative embodiment, the flow channels or pathways are interconnected to improve distribution of fluids provided or removed from the tissue site 102. The foam member 106 may be a biocompatible material that is capable of being placed in contact with the tissue site 102 and distributing reduced pressure to the tissue site 102. Examples of wound interface members may include, for example, without limitation, devices that have structural elements arranged to form flow channels, such as, for example, cellular foam, open-cell foam, porous tissue collections, liquids, gels, and foams that include, or cure to include, flow channels.

More generally, the wound interface member 118 may be porous and may be made from foam, gauze, felted mat, or any other material suited to a particular biological application. In one embodiment, wound interface member 118 comprises the foam member 106 and is a porous foam that includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. In one illustrative embodiment, the foam member 106 is a polyurethane foam—either hydrophobic or hydrophilic. The foam member 106 may be another open cell flexible polymer foam, such as a polyolefin, ethylene vinyl acetate, silicone, fluorosilicone, a fluoroelastomer, styrene, butadiene, or a thermo plastic elastomer. The foam member 106 may also be any of the other materials mentioned herein. In some situations, the foam member 106 may also be used to distribute fluids such as medications, antibacterials, growth factors, and various solutions to the tissue site 102. Other layers may be included in or on the foam member 106, such as absorptive materials, wicking materials, hydrophobic materials, and hydrophilic materials.

The foam member 106 may contain or be partially or fully saturated with a priming fluid. The priming fluid evaporates from the foam member 106 to help create a reduced pressure within the sealed space 114. As used herein, "creating of reduced pressure" or like expressions includes, without limitation, augmenting reduced pressure created or supplied by other means. The priming fluids or priming solvents may be distilled water, water treated to remove ionic content, water, or organic solvents such as alcohols and other polar solvents. In embodiments without a priming fluid, evaporation of liquids, e.g., water, from the wound alone may create the reduced pressure. In general, the evaporation of the liquids from the tissue site 102 or a priming fluid may cause a reduced pressure to be developed within the sealed space 114. As used throughout this document, "or" does not require mutual exclusivity. While the amount and nature of reduced pressure applied to a tissue site will typically vary according to the application, the reduced pressure will typically be between −5 mm Hg (−667 Pa) and −300 mm Hg (−39.9 kPa) and more typically between −75 mm Hg (−9.9 kPa) and −300 mm Hg (−39.9 kPa). For example, and not by way of limitation, the pressure may be −12, −12.5, −13, −14, −14.5, −15, −15.5, −16, −16.5, −17, −17.5, −18, −18.5, −19, −19.5, −20, −20.5, −21, −21.5, −22, −22.5, −23, −23.5, −24, −24.5, −25, −25.5, −26, −26.5 kPa or another pressure.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, quantitative values of pressure stated herein are gauge pressures. Consistent with the use herein, unless otherwise indicated, an increase in reduced pressure or vacuum pressure typically refers to a relative reduction in absolute pressure.

The wound interface member 118, e.g., foam member 106, is covered by the covering 108 to create the sealed space 114. The covering 108 has a first side 120 and a second, patient-facing side 122. The second, patient-facing side 122 of the covering 108 may be placed proximate to, or over, the foam member 106. The covering 108 may include a first portion 124 and a second portion 126. The first portion 124 may be any material that provides a fluid seal. The first portion 124 may, for example, be an impermeable or semi-permeable, elastomeric material.

"Elastomeric" means having the properties of an elastomer. Elastomers generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of the first portion 124 include a drape with adhesive on a patient-facing side, silicone drape, 3M Tegaderm® drape, or PU drape such as one available from Avery Dennison Corporation of Pasadena, Calif.

The second portion 126 of the covering 108 is the liquid-impermeable, vapor-permeable membrane 112. The liquid-impermeable, vapor-permeable membrane 112 allows vapor to exit, or egress, as suggested by arrows 116. At the same time, the liquid-impermeable, vapor-permeable material 136 allows a reduced pressure to be maintained within the container 104. The liquid-impermeable, vapor-permeable membrane 112 prevents liquid transmission. The liquid-impermeable, vapor-permeable membrane 112 is any material that is capable of preventing liquids from ingress or egress through the material and yet is operable to permit vapor, e.g., water vapor, to egress or to be transmitted through the material. Non-limiting, illustrative examples of the liquid-impermeable, vapor-permeable membrane 112 include high moisture vapor transmission rate (MVTR) films or other structures formed from hydrophilic polymers. Illustrative materials may include polyvinyl alcohol, polyvinyl acetate, cellulose based materials (ethers, esters, nitrates, etc.), polyvinyl pyrrolidone, polyurethanes, polyamides, polyesters, polyacrylates and polymethacrylates, or polyacrylamides. Vapor permeability as used with respect to the liquid-impermeable, vapor-permeable material references water vapor permeability.

The materials for the liquid-impermeable, vapor-permeable membrane 112 may be crosslinked, blended, grafted, or copolymerized with each other. The materials for the liquid-impermeable, vapor-permeable membrane 112 may be surface treated to enhance hydrophylicity. The surface treatments may include chemical, plasma, light (UV), corona, or other ionizing radiation. The material for forming the liquid-impermeable, vapor-permeable membrane 112 may also be formed by forming (e.g., casting) films and crosslinking some of the natural gums, such as guar, xanthan and alginates, or gelatin. The materials for forming the liquid-impermeable, vapor-permeable membrane 112 typically also serve as a bacteria barrier. While the material for forming the liquid-impermeable, vapor-permeable membrane 112 is fairly impervious to nitrogen and oxygen, the material is pervious to water vapor. One specific, non-limiting example of a suitable material is a 15 micron sheet of Hytrel APA60015 from DuPont E I De Nemours & Co., of Wilmington, Del.

According to one illustrative embodiment, an evaporative window 110 may be formed in the covering 108. The evaporative window 110 is any portion of the covering 108 that allows vapor egress and disallows liquid egress. In one embodiment, the material from which the covering 108 is formed allows vapor transmission, but a material or coating may be applied on or positioned adjacent to the covering 108, e.g., a patient-facing side, to inhibit the transmission of vapor through the covering at least at certain locations. For example, an adhesive may be positioned on the periphery of the covering 108 to mate the covering 108 with the tissue surrounding the wound or tissue site 102 and be omitted at the desired location of the evaporative window 110. The liquid-impermeable, vapor-permeable membrane 112 may be the same material as the covering 108 but without an adhesive or other substance that inhibits vapor transmission.

Figure 2:
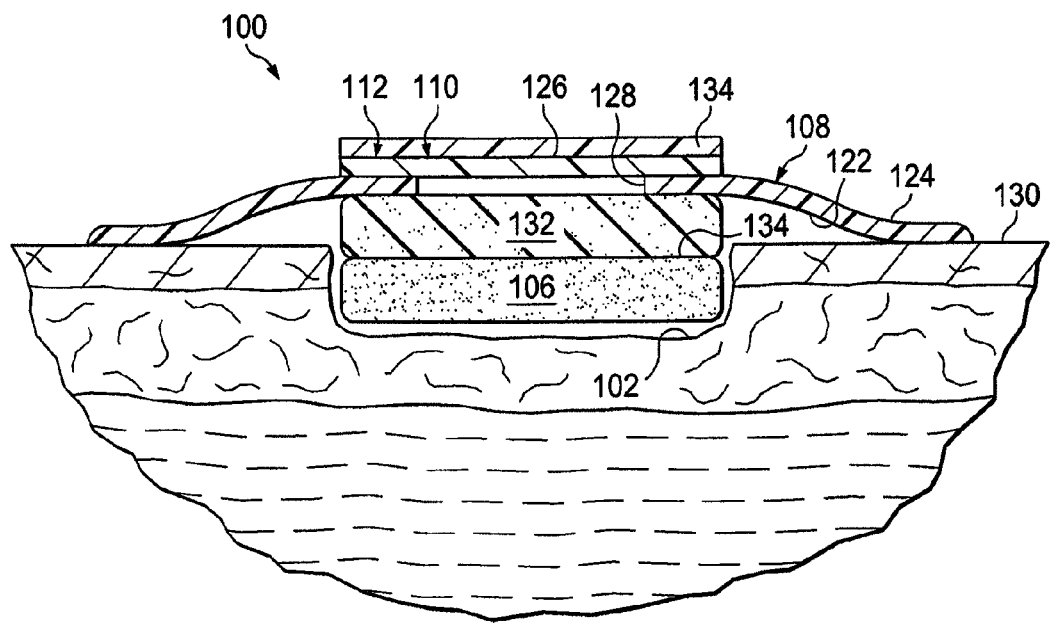
FIG. 2 is a schematic, cross section of an illustrative embodiment of a dressing for treating a tissue site wherein the dressing includes an absorbent layer and a removable release liner.

Referring to FIG. 2, an evaporative window 110 includes an evaporative-window opening, or aperture 128 (or apertures) formed in the covering 108. The evaporative-window opening or apertures 128 are covered by the liquid-impermeable, vapor-permeable membrane 112. The liquid-impermeable, vapor-permeable membrane 112 is adhered to the first portion 124 of the covering 108 over the aperture 128 to from the evaporative window 110.

According to one illustrative embodiment, a method for treating a tissue site 102 on a patient 104 includes placing the wound interface member 118, e.g., foam member 106, proximate to the tissue site 102. The first portion 124 of the covering 108 may be releasably secured to the patient's skin 130 outboard of the tissue site 102 being treated. The covering 108 is used to form the sealed space 114 over the tissue site 102. Liquids from the tissue site 102 are drawn into the foam member 106 by the hydrophilic nature of the foam member 106 and by the creation of reduced pressure from the evaporation of a priming liquid inside of the foam member 106. As the priming liquid evaporates, a reduced pressure may be created in the sealed space 114. In one illustrative embodiment, evaporation of the priming liquid or body fluid creates reduced pressure such that no external source of reduced pressure is utilized and yet reduced pressure adequate for therapy is applied to the sealed space 114. The evaporated liquids, or vapor, from the tissue site 102 or the evaporated priming liquid, exit the sealed space 114 through the liquid-impermeable, vapor-permeable membrane 112.

Because of the evaporation of liquids from the tissue site 102, the dressing 100 is able to receive and process more liquids over time than the dressing 100 is capable of retaining at one time. For example, in one illustrative embodiment, the dressing 100 holds 30 cc of liquid, i.e., the dressing 100 becomes completely saturated with 30 cc of liquid, but with evaporation, may receive over time 40 cc of liquid. In this example, the dressing 100 processes 133 percent of capacity measured by saturation capacity. In other embodiments, the dressing 100 may process 110%, 120%, 130%, 140%, 150%, 160%, or more of capacity based on saturation capacity.

Referring primarily to FIG. 2, an illustrative embodiment of a dressing 100 for treating a tissue site 102 is presented. The dressing 100 of FIG. 2 is the same as the dressing 100 of FIG. 1 with two main modifications. First, an absorbent layer 132 has been disposed between the second, patient-facing side 122 of the covering 108 and the first side 107 of the foam member 106. The absorbent layer 132 may be any layer of material for receiving and storing liquids, such as, an ionic type, which is based on cross linked acrylic, methacrylic, and sulphonated acrylic polymers. The absorbent layer 132 may also be a non-ionic type, which is based on water soluble polymers, such as alginates, carboxymethy cellulose, polyvinyl pyrrolidone, or other absorbent material. The absorbent layer 132 receives and retains fluids from the tissue site 102 and enhances the capacity of the dressing 100. Other layers, including a wicking layer (not shown) may be added as well. If a wicking layer is added, it pulls liquids and retains them at a desired location. For example, the wicking layer may pull liquids and retain the liquids against the liquid-impermeable, vapor-permeable membrane.

The second main difference is the inclusion of a removable release liner 134, or activation layer. The removable release liner 134 provides a barrier to vapor that might otherwise egress through the liquid-impermeable, vapor-permeable membrane 112. The removable release liner 134 allows a priming fluid to be in the foam member 106 prior to use and yet not evaporate until the removable release liner 134 is removed.

Figure 3:
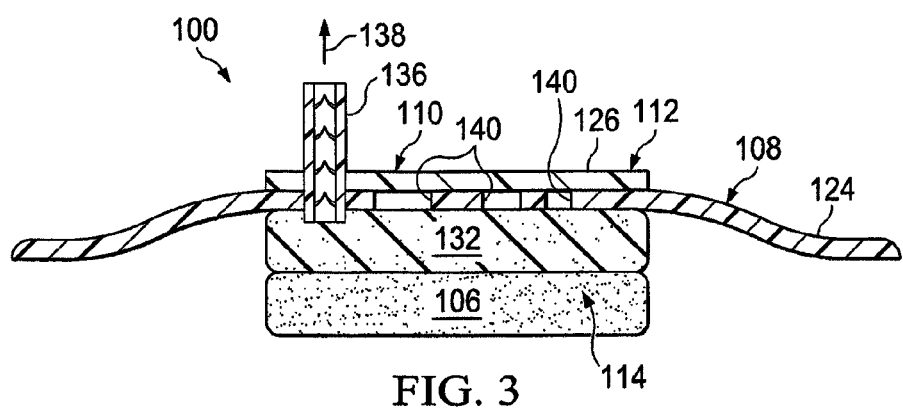
FIG. 3 is a schematic, cross section of an illustrative embodiment of a dressing for treating a tissue site wherein the dressing includes a one-way valve.

Referring now primarily to FIG. 3, an illustrative embodiment of a dressing 100 for treating a tissue site, such as tissue site 102 in FIGS. 1 and 2, is presented. The dressing 100 of FIG. 3 is analogous to the dressing 100 of FIG. 1 except for two main differences. First, a one-way valve 136 is included. The one-way valve 136 extends through a covering 108 and into a sealed space 114. The one-way valve 136 may also extend through a liquid-impermeable, vapor-permeable membrane 112. When the covering 108 is pressed towards the tissue site 102 (FIG. 1), the air in the sealed space 114 is evacuated through the one-way valve 136 as suggested by arrow 138. The removal of air or other gasses from within the sealed space 114 helps to develop a reduced pressure in the sealed space 114. The evacuation of the gases through the one-way valve 136 or the evaporation and egress of liquids from the sealed space creates reduced pressure in the sealed space 114. A reduced pressure treatment may, thus, occur at the tissue site without requiring a separate reduced-pressure source.

In the embodiment of FIG. 3, the covering 108 includes a plurality of apertures 140, or evaporative-window openings, that comprise the evaporative window 110. The apertures 140 are covered by the liquid-impermeable, vapor-permeable membrane 112 to form the evaporative window 110. With respect to the second difference, the embodiment of FIG. 3 also includes an absorbent layer 132.

Figure 4:
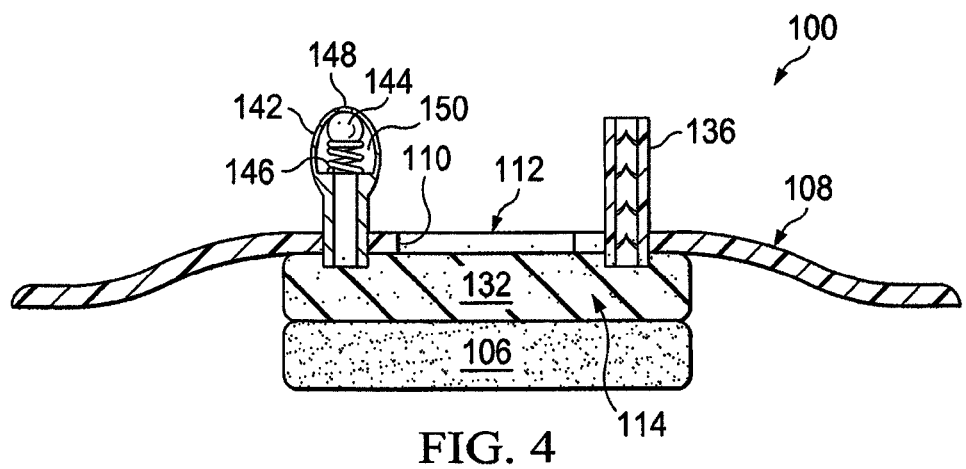
FIG. 4 is a schematic, cross section of an illustrative embodiment of a dressing for treating a tissue site wherein the dressing includes a pressure-regulating valve and a one-way valve.

Referring now primarily to FIG. 4, an illustrative embodiment of a dressing 100 for treating a tissue site, such as tissue site 102 in FIGS. 1 and 2, is presented. The dressing 100 of FIG. 4 is similar to the dressing 100 in FIG. 1, but includes a one-way valve 136 and also includes a pressure-regulating valve 142. The one-way valve 136 extends through the covering 108 and into the sealed space 114 as in FIG. 3, and the pressure-regulating valve 142 also extends through the covering 108 and into the sealed space 114.

The pressure-regulating valve 142 allows ambient pressure or ambient air to enter into the sealed space 114 when a maximum reduced pressure value is reached within the sealed space 114. The introduction of the ambient air lowers the reduced pressure and keeps the reduced pressure below a maximum value. The pressure-regulating valve 142 may take numerous forms, but is shown as having a ball 144 with a biasing member 146 that biases the ball 144 against an aperture 148. When the reduced pressure communicated into a chamber 150 from the sealed space 114 is high enough to cause the ball 144 to become unseated from the aperture 148, air is introduced into the chamber 150 and the air is communicated into the sealed space 114. Through this action, the pressure within the sealed space 114 may be regulated to be below a maximum reduced-pressure value.

Figure 5:
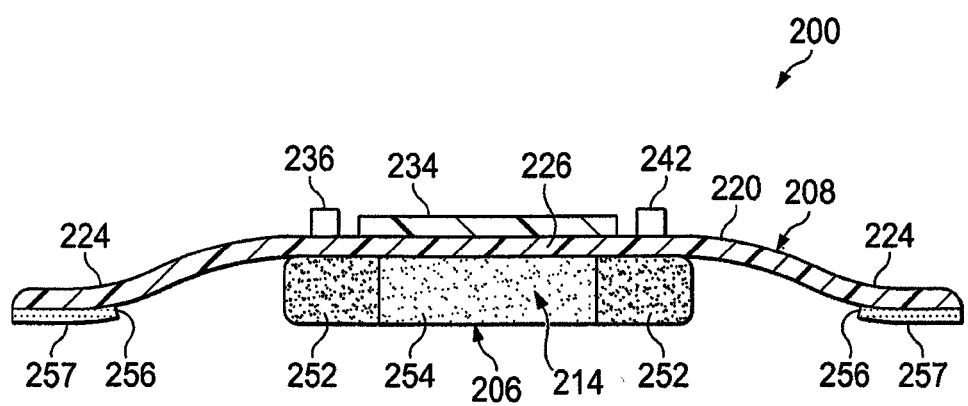
FIG. 5 is a schematic, cross section of an illustrative embodiment of a dressing for treating a tissue site wherein the dressing includes a first foam and a second foam.

Referring now primarily to FIG. 5, an illustrative embodiment of a dressing 200 is presented. The dressing 200 is analogous to dressing 100 of FIG. 1 in many respects. In this embodiment, however, the dressing 200 includes a foam member 206 that comprises a first foam 252 and a second foam 254. The first foam 252 may be an annular member having a first rigidity. The second foam 254 may be a circular insert that goes into an annular interior portion of the first foam 252 and that has a second rigidity. The first rigidity is greater than the second rigidity. Thus, when under reduced pressure, the second foam 254 will collapse more readily than the first foam 252. The more rigid first foam 252 may help to develop a vacuum within a sealed space 214 by serving as an internal biasing member that forces a covering 208 away from the patient.

The foam member 206 is covered with the covering 208 that extends beyond the margins of the tissue site being treated. The covering 208 has a first portion 224 and a second portion 226. The first portion 224 of the covering 208 is typically outboard of the foam member 206. The covering 208 may be secured to the patient's skin using an attachment device 256, such as an adhesive or hydrocolloid. The attachment device 256 may have a release liner covering a patient facing side 257 before deployment. The covering 208 itself may be a liquid-impermeable, vapor-permeable material, and at least a second portion 226 has no adhesive or other substances that might impair vapor transmission.

A priming liquid may be disposed within the foam member 206. In order to prevent premature evaporation of the priming liquid before the dressing 200 is deployed on a tissue site, a removable release liner 234 may be releasably attached to a first side 220 of the covering 208 over the second foam 254. The removable release liner 234 may be the same size or larger than the foam member 206. The removable release liner 234 is removed at the time of deployment on a patient. Analogous to dressing 100 of FIG. 4, the dressing 200 may include a one-way valve 236 and a pressure-regulating valve 242.

Still referring to FIG. 5, in operation according to one illustrative embodiment, the foam member 206 is placed proximate to the tissue site, such as tissue site 102 of FIG. 1, that is to be treated. If not already done, the cover 208 is placed over the foam member 206 and the attachment device 256 is used to secure the covering 208 to the patient's skin. The removable release liner 234 may be removed. The dressing 200 may be physically primed by depressing the dressing 200 toward the tissue site to cause at least the second foam 254 to partially collapse forcing air through the one-way valve 236 to place an initial reduced pressure into the sealed space 214. The reduced pressure within sealed space 214 is further enhanced as liquids from the tissue site or the priming fluid evaporate and egress through the second portion 226 of the covering 208.

Figure 6:
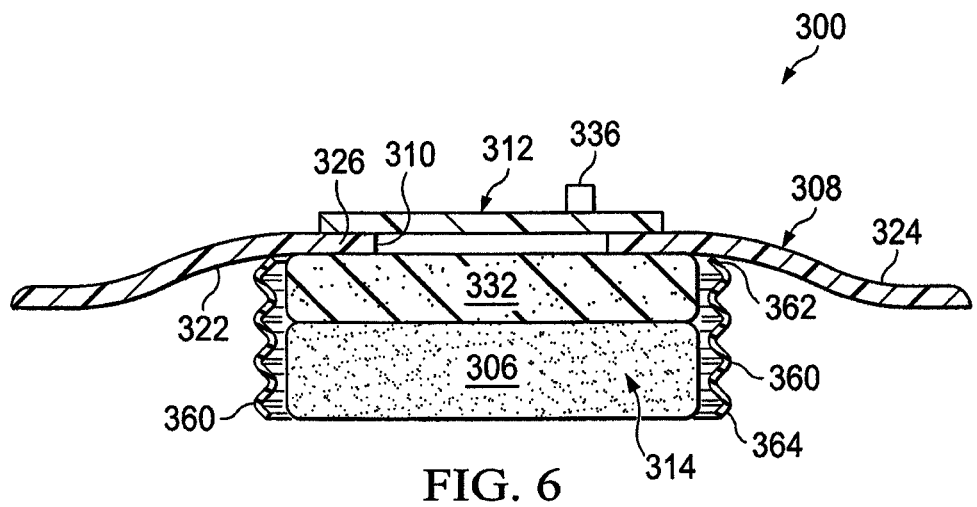
FIG. 6 is a schematic, cross section of an illustrative embodiment of a dressing for treating a tissue site wherein the dressing includes bellows.

Referring now primarily to FIG. 6, an illustrative embodiment of a dressing 300 is presented. The dressing 300 is analogous in most respects to the dressing 100 of FIG. 2. The dressing 300 includes a foam member 306 for placing proximate to a tissue site, such as tissue site 102 in FIG. 1, and an absorbent layer 332 for receiving and retaining liquids from the tissue site. The foam member 306 and absorbent layer at 332 are covered by a covering 308. The covering 308 forms a sealed space 314 over the tissue site and the foam member 306. The covering 308 has a first portion 324 and a second portion 326. The second portion 326 includes an evaporative window 310. A liquid-impermeable, vapor-permeable membrane 312 is associated with the evaporative window 310 and allows the egress of evaporated liquids from within the sealed space 314 to an exterior of the dressing 300. A one-way valve 336 extends from an exterior of the dressing 300 into the sealed space 314 and allows gas within the sealed space 314 to exit the one-way valve 336 but disallows gas from entering.

The dressing 300 further includes a biasing member that when in position biases the covering 306 away from the patient. For example, the biasing member may comprise bellows 360 having a first end 362 and a second end 364. The first end 362 engages a tissue-facing side 322 of the covering 306 and the second end 364 engages the patient's skin (not shown). In operation according to one illustrative embodiment, after deploying the dressing 300, the dressing 300 may be pressed against the patient causing air in the sealed space 314 to exit the one-way valve 336 and simultaneously to cause biasing member, e.g., the bellows 360, to at least partially collapse or compress. When at least partially compressed, the bellows 360 seek to return to their free or natural position and thereby place a force on the covering 306 that pulls the covering 308 away from the patient. This action helps to create a vacuum (or greater reduced pressure) within the sealed space 314.

Figure 7:
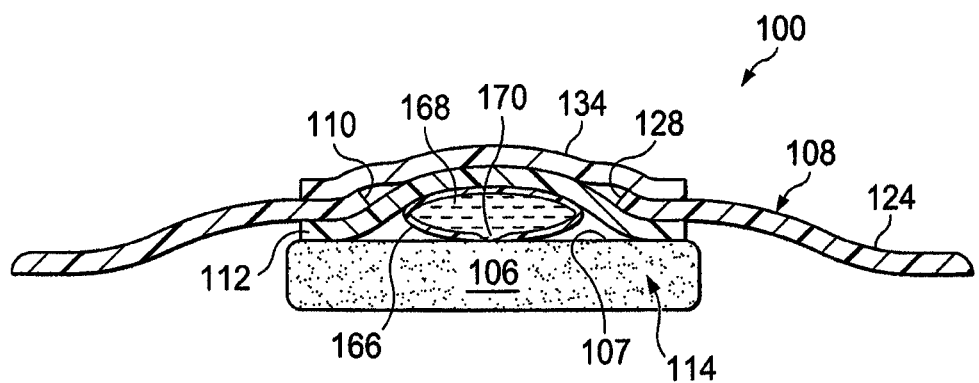
FIG. 7 is a schematic, cross section of an illustrative embodiment of a dressing for treating a tissue site wherein the dressing includes a container with a priming fluid.

Referring now primarily to FIG. 7, an illustrative embodiment of a dressing 100 is presented. The dressing 100 is analogous to the dressing 100 of FIG. 1 in most respects. In this embodiment, however, a container 166 containing a priming fluid 168 is disposed on a first side 107 of a foam member 106. The container 166 may include a weakened portion 170 that is adapted to fail before other portions of the container 166. In other embodiments, any type of valve may be included in lieu of the weakened portion 170, wherein the valve retains the primary fluid until the priming fluid is needed and then allows the priming fluid out under the influence of reduced pressure.

A covering 108 may cover the foam member 106 and form a sealed space 114. The cover 108 includes an evaporative window 110 formed with an aperture 128, or evaporative-window opening. The evaporative window 110 includes a liquid-impermeable, vapor-permeable membrane 112 that covers the aperture 128 and extends beyond the aperture 128 in this illustrative embodiment. Thus, a portion of the liquid-impermeable, vapor-permeable membrane 112 is disposed between the first portion 124 of the covering 108 and the foam member 106. A removable release liner 134 may cover the evaporative window 110 until time for use.

Still referring primarily to FIG. 7, according to one illustrative embodiment, in operation, the foam member 106 is placed proximate to the tissue site to be treated and the covering 108 is placed over the foam member 106 and secured to the patient's skin around the tissue site. The container 166 may then be ruptured by depressing the container 166 or alternatively, may have already been ruptured against a hard surface or by other means immediately before placing on the tissue site. Once ruptured, the container 166 releases the priming fluid 168 onto the foam member 106. In some embodiments, the weakened portion 170 may be included to control the point of rupture. The removable release liner 134 is removed from the evaporative window 110. The evaporative process may then begin helping to create a reduced pressure within the sealed space 114.

In another illustrative embodiment, a micro-pump, e.g., a piezoelectric pump, is included under (for the orientation shown in FIG. 1) the covering 108. The micro-pump creates reduced pressure in the sealed space 114. The exhaust from the micro-pump may egress through the liquid-impermeable, vapor-permeable material of the evaporative window 110. Alternatively or in addition, the exhaust may egress through a specific outlet or one-way valve.

Figure 8:
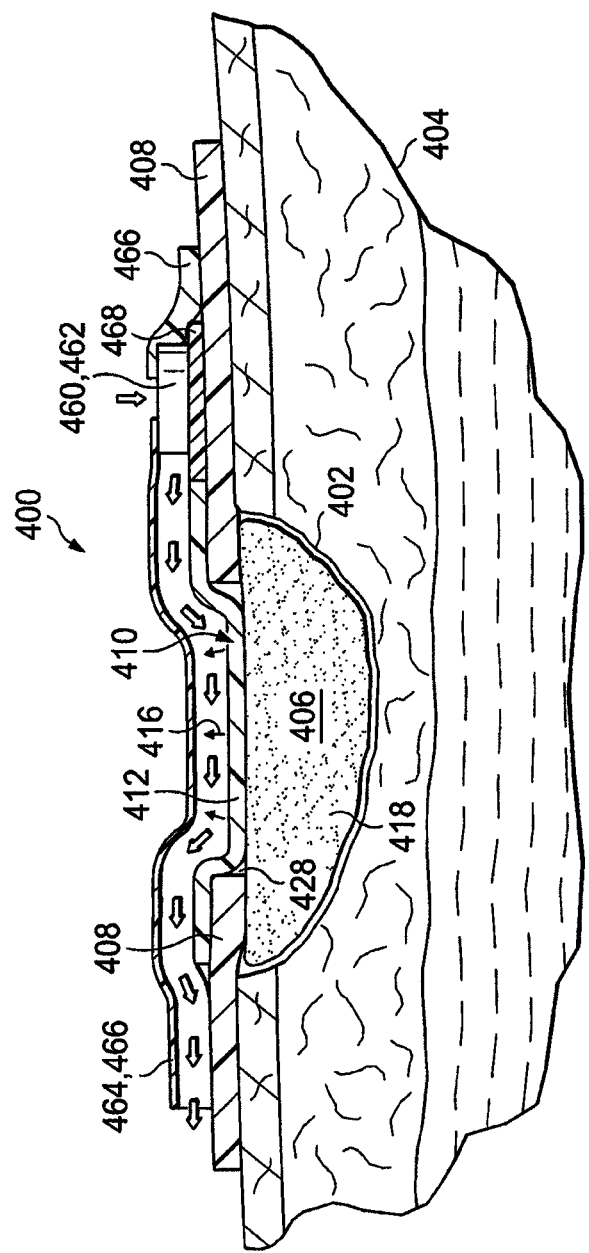
FIG. 8 is a schematic, cross section of an illustrative embodiment of a dressing for treating a tissue site.

Referring primarily to FIG. 8, a dressing 400 for treating a tissue site 402 on a patient 404 is presented. The dressing 400 is analogous in most respects to dressing 100 of FIG. 1, except a forced-air device 460 has been added. The dressing 400 includes, inter alia, a covering 408 that allows evaporated liquids to egress the dressing 400. At least a portion of the covering 408 comprises a liquid-impermeable, vapor-permeable membrane 412. For example, an evaporative-window opening or aperture 428 may be formed through the covering 408, and the aperture 428 may be covered by the liquid-impermeable, vapor-permeable membrane 412 to form an evaporative window 410. The covering 408 forms a sealed space 414 over the tissue site 102 and a wound interface member 418, e.g., a foam member 406. The liquid-impermeable, vapor-permeable membrane 412 is operable to allow liquids, e.g., water, in the sealed space 414 that have evaporated to egress the sealed space 414 as suggested by arrows 416.

The forced-air device 460 may be any device that moves air across the liquid-impermeable, vapor-permeable membrane 412 to increase the rate of water vapor transport. The forced air may be intermittent or continuous. The forced-air device 460 may be a fan, an electrostatic device, or a piezoelectric pump 462. Flexible baffling 464 may be formed over the liquid-impermeable, vapor-permeable membrane 412 and is fluidly coupled to the piezoelectric pump 462 for receiving air from or delivering air to the piezoelectric pump 462. Drape tape 466 or another device may used to help couple the piezoelectric pump 462 to the covering 408. The piezoelectric pump 462 may be positioned on a cushioning member 468. The flexible baffles 464 may be any device that helps channel air from or to the piezoelectric pump 462 over the liquid-impermeable, vapor-permeable membrane 412. For example, the flexible baffling 464 may be an inflatable passageway 466 formed over the liquid-impermeable, vapor-permeable membrane 412 and held by an adhesive (not shown) against at least a portion of the liquid-impermeable, vapor-permeable membrane 412.

It should be understand that all the dressings presented herein may be formed on site or may be pre-assembled. The pre-assembled embodiments may be packaged within a sealed package.

Although the present invention and its advantages have been disclosed in the context of certain illustrative embodiments, it should be understood that various changes, substitutions, permutations, and alterations can be made without departing from the scope of the invention as defined by the appended claims. As an illustrative, non-limiting example, components from one embodiment may be used with components of other embodiments presented. As a non-limiting example, the one-way valve 136 of FIG. 4 may be added to the dressing 100 of FIG. 7. As another non-limiting example, the forced-air device 460 of FIG. 8 may be added to any of the other embodiments. As yet another non-limiting example, the release liner 134 may be applied to any of the embodiments herein.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A dressing for treating a tissue site, the dressing comprising:
   a covering configured to cover the tissue site to form a sealed space;
   a membrane forming at least a portion of the covering and configured to permit evaporation of water vapor through the membrane;
   a release liner releasably coupled to the covering proximate to the membrane; and
   an adhesive disposed on at least a portion of the covering, the membrane being free of adhesive.

2. The dressing of claim 1, further comprising a one-way valve coupled to the covering.

3. The dressing of claim 2, wherein the one-way valve permits fluid flow from the sealed space through the covering.

4. The dressing of claim 1, further comprising a pressure-regulating valve coupled to the covering.

5. The dressing of claim 4, wherein the pressure-regulating valve permits fluid flow into the sealed space through the covering.

6. The dressing of claim 5, wherein the pressure-regulating valve permits fluid flow into the sealed space in response to a maximum reduced pressure in the sealed space.

7. The dressing of claim 1, further comprising a wound interface layer configured to be positioned between the covering and the tissue site.

8. The dressing of claim 7, wherein the wound interface layer comprises a foam member.

9. The dressing of claim 7, wherein the wound interface layer comprises a gauze.

10. The dressing of claim 7, further comprising an absorbent layer configured to be disposed between the wound interface member and the covering.

11. The dressing of claim 10, further comprising a priming fluid in the absorbent layer.

12. The dressing of claim 7, further comprising a priming fluid in the wound interface member.

13. The dressing of claim 1, further comprising an absorbent layer configured to be disposed between the tissue site and the covering.

14. The dressing of claim 1, further comprising:
a container disposed between the covering and the tissue site, the container having a weakened portion configured to fail before other portions of the container; and
a priming fluid disposed in the container.

15. The dressing of claim 1, further comprising a foam member disposed between the covering and the tissue site, the foam member comprising:
a first foam having an aperture;
a second foam disposed within the aperture of the first foam; and
wherein the first foam is more rigid than the second foam.

16. The dressing of claim 1, further comprising:
a first foam member having an annular shape and disposed between the covering and the tissue site; and
a second foam member disposed within the first foam member, wherein the first foam member is more rigid than the second foam member.

17. The dressing of claim 1, further comprising:
a foam member configured to be disposed between the covering and the tissue site; and
a biasing member disposed around the foam member.

18. The dressing of claim 17, wherein the biasing member comprises a bellows.

19. The dressing of claim 1, further comprising a forced-air device associated with the covering configured to force air across the membrane.

20. The dressing of claim 19, wherein the forced-air device comprises a piezoelectric pump, the dressing further comprising a flexible baffling disposed proximate to the covering on a side opposite the tissue site, the flexible baffling configured to direct air across the membrane.

21. The dressing of claim 19, further comprising an inflatable passageway disposed adjacent to the membrane and fluidly coupled to the forced-air device.

22. The dressing of claim 1, wherein the membrane includes a surface having a hydrophilic treatment.

23. The dressing of claim 22, wherein the hydrophilic treatment comprises an ionizing radiation.

24. The dressing of claim 1, further comprising:
a foam member configured to be disposed between the tissue site and the covering; and
a micro-pump disposed between the foam member and the covering.

25. A method for treating a tissue site with reduced pressure, the method comprising:
deploying a foam member proximate to the tissue site;
covering the foam member with a covering having an evaporative window to form a sealed space over the foam member; and
evaporating liquids in the sealed space through the evaporative window to generate reduced-pressure.

26. The method of claim 25, wherein a priming fluid is disposed in the foam member.

27. The method of claim 25, wherein a one-way valve is associated with the covering and the method further comprises depressing the foam member to remove air through the one-way valve from the sealed space.

28. The method of claim 25, further comprising opening a pressure-regulating valve coupled to the covering in response to a maximum reduced pressure in the sealed space.

29. The method of claim 25, further comprising removing a release liner covering the evaporative window.

30. The method of claim 25, further comprising:
disposing a container storing a priming fluid between the covering and the foam member; and
rupturing the container to release the priming fluid into the sealed space.

31. The method of claim 25, further comprising forcing air across the evaporative window with a forced-air device.

32. A method of manufacturing a dressing for treating a tissue site, the method comprising:
providing a foam member for placing proximate to the tissue site;
providing a covering formed with an opening; and
associating a membrane with the opening to form an evaporative window, the membrane being configured to permit liquids to evaporate through the covering.

33. The method of claim 32, further comprising the step of applying a removable release liner over the membrane.

34. The method of claim 32, further comprising introducing a priming fluid into the foam member.

35. The method of claim 32, further comprising disposing a container having a priming fluid on a side of the covering.

36. The method of claim 32, further comprising coupling a pressure-regulating valve to the covering.

37. The method of claim 32, further comprising coupling a one-way valve to the covering.

38. The method of claim 32, further comprising coupling a one-way valve to the covering and coupling a pressure-regulating valve to the covering.

* * * * *